(12) United States Patent
Massie

(10) Patent No.: US 7,993,000 B2
(45) Date of Patent: Aug. 9, 2011

(54) METHOD AND APPARATUS FOR IMAGING AN EYE OF A SMALL ANIMAL

(75) Inventor: Norbert A. Massie, San Ramon, CA (US)

(73) Assignee: Phoenix Research Laboratories, San Ramon, CA (US)

( * ) Notice: Subject to any disclaimer, the term of this patent is extended or adjusted under 35 U.S.C. 154(b) by 0 days.

(21) Appl. No.: 12/138,575

(22) Filed: Jun. 13, 2008

(65) Prior Publication Data

US 2008/0309876 A1 Dec. 18, 2008

Related U.S. Application Data

(60) Provisional application No. 60/944,353, filed on Jun. 15, 2007.

(51) Int. Cl.
*A61B 3/10* (2006.01)
*A61B 3/00* (2006.01)

(52) U.S. Cl. .................. 351/214; 351/246; 351/219

(58) Field of Classification Search .............. 351/219, 351/205, 246, 214, 206–207
See application file for complete search history.

(56) References Cited

U.S. PATENT DOCUMENTS

| | | | |
|---|---|---|---|
| 3,770,342 A | 11/1973 | Dudrange | |
| 3,944,341 A | 3/1976 | Pomerantzeff | |
| 4,026,638 A | 5/1977 | Govignon | |
| 4,135,791 A | 1/1979 | Govignon | |
| 4,200,362 A | 4/1980 | Pomerantzeff | |
| 4,265,518 A * | 5/1981 | Matsumura | 351/206 |
| 4,411,502 A | 10/1983 | Lang et al. | |
| 4,423,932 A | 1/1984 | Takahashi | |
| 4,443,075 A | 4/1984 | Crane | |
| 4,728,183 A * | 3/1988 | Heacock et al. | 351/219 |
| 4,753,526 A * | 6/1988 | Koester | 351/219 |
| 4,781,453 A | 11/1988 | Kobayashi | |
| 5,152,295 A | 10/1992 | Kobayashi et al. | |
| 5,186,173 A * | 2/1993 | Zuckerman | 351/205 |

(Continued)

FOREIGN PATENT DOCUMENTS

EP 0337745 10/1989

(Continued)

OTHER PUBLICATIONS

International Search Report, WO 2008/157359 (Jan. 8, 2009) 3 pages.

(Continued)

*Primary Examiner* — Darryl J Collins
*Assistant Examiner* — Zachary Wilkes
(74) *Attorney, Agent, or Firm* — Kirton & McConkie

(57) ABSTRACT

Imaging an eye of an animal can include injecting a ring of light through an outer portion of an entrance pupil of the eye of the animal onto a back interior portion of the eye. Light reflected off of the back interior portion of the eye and through an exit pupil effectively located at the entrance pupil within the ring of light can be collected. A diameter of the exit pupil at the entrance pupil can be less than an inner diameter of the ring of light, and a difference between an outer diameter of the ring and the inner diameter of the ring can be at least twenty percent of a diameter of the eye. The collected light reflected off of the back interior portion of the eye can be focused to thereby form an image of the back interior portion of the eye.

32 Claims, 11 Drawing Sheets

U.S. PATENT DOCUMENTS

| | | | |
|---|---|---|---|
| 5,303,709 | A | 4/1994 | Dreher et al. |
| 5,394,199 | A | 2/1995 | Flower |
| 5,537,162 | A | 7/1996 | Hellmuth et al. |
| 5,543,865 | A * | 8/1996 | Nanjo ............................ 351/206 |
| 5,608,472 | A | 3/1997 | Szirth et al. |
| 5,684,561 | A | 11/1997 | Yancey |
| 5,719,659 | A | 2/1998 | Suzuki |
| 5,822,032 | A | 10/1998 | Edwards et al. |
| 5,900,928 | A | 5/1999 | Riva et al. |
| 6,027,216 | A | 2/2000 | Guyton et al. |
| 6,309,070 | B1 | 10/2001 | Svetliza et al. |
| 6,361,167 | B1 | 3/2002 | Su et al. |
| 6,394,603 | B2 | 5/2002 | Miwa et al. |
| 6,540,357 | B1 | 4/2003 | Ohnuma et al. |
| 6,685,317 | B2 | 2/2004 | Su et al. |
| 6,814,441 | B2 | 11/2004 | Ohnuma et al. |
| 6,921,169 | B2 | 7/2005 | Su et al. |
| 7,121,665 | B2 | 10/2006 | Su et al. |
| 2003/0048929 | A1 | 3/2003 | Golden et al. |
| 2004/0263781 | A1 * | 12/2004 | Suzuki et al. .................. 351/206 |
| 2007/0030446 | A1 | 2/2007 | Su et al. |

FOREIGN PATENT DOCUMENTS

| | | |
|---|---|---|
| WO | WO 03/009745 | 2/2003 |
| WO | 2006/016366 | 2/2006 |
| WO | WO 2008/138953 | 11/2008 |

OTHER PUBLICATIONS

International Preliminary Report on Patentability, WO 2008/157359 (Dec. 17, 2009) 4 pages.

Written Opinion of International Searching Authority, WO 2008/157359 (Jan. 8, 2009) 3 pages.

Paques et al., "Panretinal, High-Resolution Color Photography of the Mouse Fundus," Investigative Ophthalmology & Visual Science, vol. 48, No. 6 (Jun. 2007) pp. 2769-2774.

Hawes et al., "Mouse fundus photography and angiography: A catalogue of normal and mutant phenotypes," Molecular Vision, 5:22 (1999), 8 pages.

Sommer, et al., "Cross-Polarization Photography of the Nerve Fiber Layer", Arch Opthalmol article, vol. 102, Jun. 1984.

Fariza, et al., "Use of Circularly Polarized Light in Fundus and Optic Disc Photography", Arch Opthalmol, vol. 106, Jul. 1988.

Eli Peli, M.Sc., O.D., "Circular Polarizers Enhance Visibility of Ednothelium in Specular Reflection Biomicroscopy", Arch Opthalmol article, vol. 103, May 1985.

Mellem-Kairala, et al., "Improved Contrast of Peripapillary Hyperpigmentation Using Polarization Analysis", Investigative Opthalmology & Visual Science, Mar. 2005, vol. 46, No. 3.

Hochheimer et al., "Retinal Polarization Effects", Applied Optics, vol. 21, No. 21, Nov. 1, 1982.

Kawara, et al., "A New Method for Retroillumination Photography of Cataractous Lens Opacities", American Journal of Opthalmology, vol. 90, No. 2, pp. 186-189, 1980.

Bueno, et al., "Polarization and Retinal Image Quality Estimates in the Human Eye", Optical Society of America, vol. 18, No. 3, Mar. 2001.

Unicare, "Opthalmologic Techniques for Evaluating Glaucoma", Medical Policy, http://medpolicy.unicare.com/policies/MED/glaucoma.html, Aug. 1, 2006.

Saine et al., "Fundus Photography: Instrumentation and Technique," Butterworth-Heinemann (1997), pp. 15-17, 27, 28, and 65-77.

MediVision 510(k) premarket notification and letter from Department of Health & Human Services, Oct. 20, 2006.

PCT/US2008/066931: International Preliminary Report on Patentability (Dec. 30, 2009) (5 pages).

Supplemental European Support Report, EP Application No. 08771029.9, 7 pages. (Apr. 4, 2011).

* cited by examiner

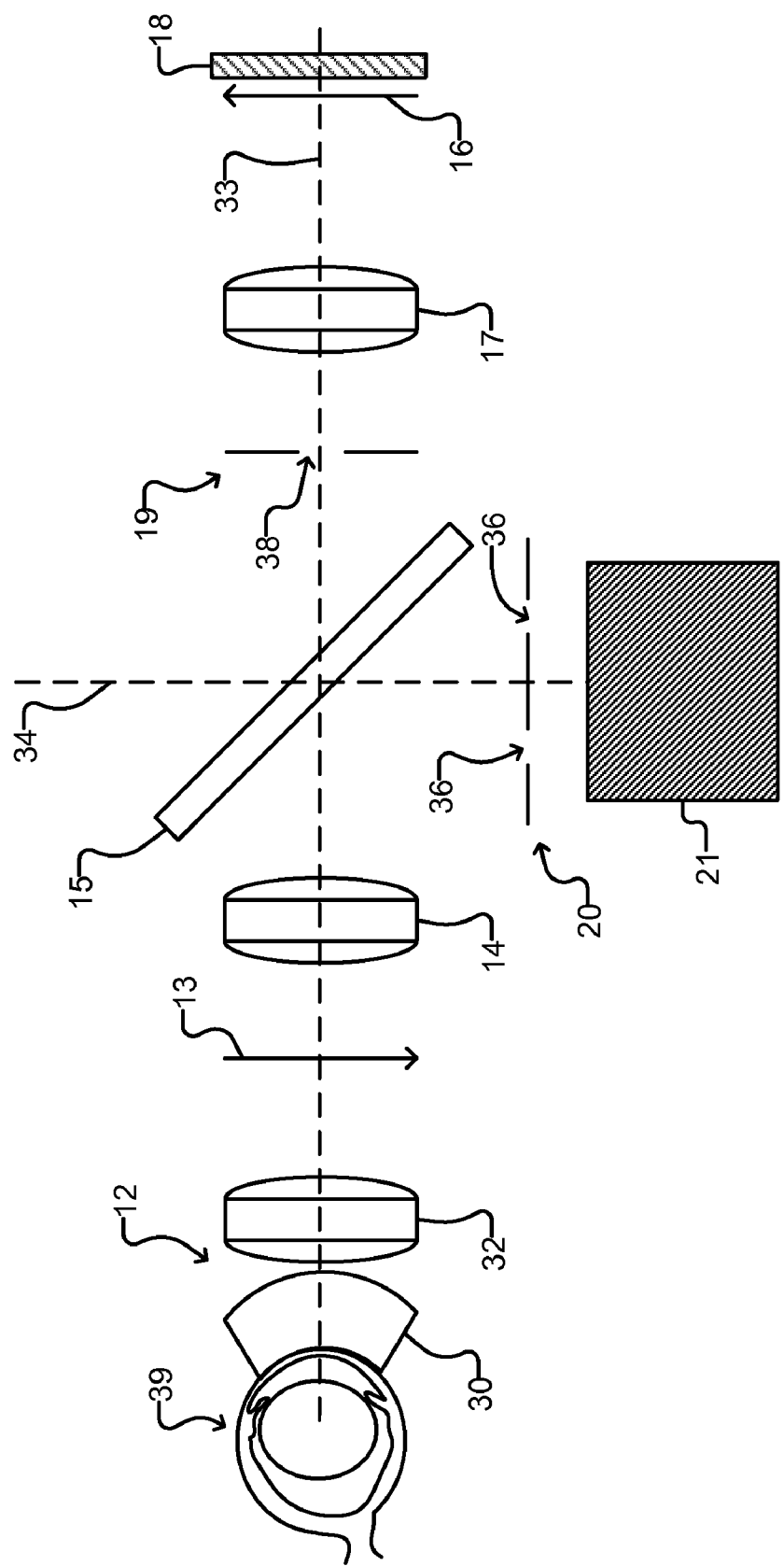

METHOD AND APPARATUS FOR IMAGING AN EYE OF A SMALL ANIMAL

CROSS REFERENCE TO RELATED APPLICATIONS

This application claims the benefit of U.S. Provisional Patent Application 60/944,353, which was filed Jun. 15, 2007.

BACKGROUND

Small animals such as rodents are used extensively in clinical research. Some rodents, particularly certain mice and rats, are acceptable genetic analogues to humans and are subjects for tests of drug and genetic therapies as well as other tests. To this end there is a critical need to image the back of the eye. This imaging is needed both to test therapies for eye diseases and to detect the ocular side effects of drugs administered for other diseases. In this later instance it is possible to add a fluorescent tag to the drug to detect its presence in the eye.

The mouse eye is typically about 3 millimeters in diameter and the rat eye is typically about 6 millimeters in diameter, this compared to the average human eye at about 25 millimeters in diameter. As a result of the tiny size of the rodent eye, the use of standard human eye imaging systems for rodents is difficult or impossible. Even when conventional cameras produce images, they are limited in resolution, field of view, and are very difficult to use.

There is a substantial need for wide-field and high resolution imaging of the rodent eye (which can be in color) with the option for fluorescent angiography and fluorescent imaging (auto-fluorescence) and with means suitable for every day use in a production environment because many studies involve large numbers of animals.

In FIG. 2 is shown at the same scale the eye of the human 8 and an eye 39 of a mouse. The rat eye has the same general features as the mouse eye but is about 6 millimeters in diameter. Besides the substantial difference in size the eyes of the human and rodent differ in other significant features and in FIG. 3 the eye 39 of a mouse is shown at an expanded scale to show details. First, most of the refractive power of the human eye is in the protruding cornea 10 whereas in the rodent eye, which is nearly spherical, the large crystalline 11 lens provides most of the refractive power. Second, the human eye is recessed so that the bones about the eye can protect the eye from mechanical injury whereas the rodent eye protrudes from the head. Third, the eyes of the rodent are located more on the side of the head rather than frontally as in the human. Fourth, the human eye can only dilate so that at best the optical system is f/3 whereas the rodent can dilate to nearly f/1.3.

There is currently no known imaging system specifically designed for imaging the back of the rodent eye. Cameras designed for use with human subjects usually image at a stand off distance of 10 cm. These cameras require a cooperative subject who will place their head in a chin/forehead rest. And, the minimum pupil diameter requirement for the so-called "non-mydriatic" cameras is 4 millimeters. The largest dilation with the larger rat eye is 4 millimeters and with the mouse 2 millimeters but the curvature of the back of the rat eye has a diameter of 6 millimeters whereas that of the human eye has a curvature of 25 millimeters diameter. Accordingly, only a small portion of an image of an eye 39 of a mouse or rat will be in focus. Indeed images of the rat eye are obtained but with great difficulty in university settings and the images are of very poor quality. Similar results and limitations apply to the use of the scanning laser ophthalmoscope (SLO) to this problem and the SLO does not provide for color imaging.

Although the invention is not limited to the following features and advantages, some embodiments of the invention can provide the following: wide-field, high resolution imaging of the back of the rodent eye with the option of providing fluorescent angiography and fluorescent imaging (auto-fluorescence); versatility to image mice, rats, and larger animals such as rabbits and monkeys; and images at fields of view (FOV) of at least 60 degrees and with resolutions below 5 microns.

SUMMARY

In some embodiments, a method of imaging an eye of an animal can include injecting a ring of light through an outer portion of an entrance pupil of the eye of the animal onto a back interior portion of the eye. The method can also include collecting light reflected off of the back interior portion of the eye and through an exit pupil effectively located at the entrance pupil within the ring of light. A diameter of the exit pupil at the entrance pupil can be less than an inner diameter of the ring of light, and a difference between an outer diameter of the ring and the inner diameter of the ring can be at least twenty percent of a diameter of the eye. The method can further include focusing the collected light reflected off of the back interior portion of the eye and thereby forming an image of the back interior portion of the eye.

In some embodiments, an apparatus for imaging an eye of an animal can include a light source configured to generate a ring of light and a contact lens configured to contact the eye of the animal and inject the ring of light through an outer portion of an entrance pupil of the eye onto a back interior portion of the eye. A difference between an outer diameter of the ring and the inner diameter of the ring can be at least twenty percent of a diameter of the eye, and a diameter of the exit pupil at the entrance pupil can be less than an inner diameter of the ring of light. The apparatus can further include an optical system configured to relay the ring of light generated by light source to the contact lens. The optical system can be further configured to collect light reflected off of the back interior portion of the eye and through an exit pupil effectively located at the entrance pupil within the ring of light. The optical system can also be configured to focus the collected light reflected off of the back interior portion of the eye and thereby form an image of the back interior portion of the eye.

BRIEF DESCRIPTION OF THE DRAWINGS

FIG. 5: A schematic diagram of an exemplary embodiment of an imaging system is shown.

FIG. 6b: Shows a front view of the light ring generated by the module of FIG. 6a.

DETAILED DESCRIPTION OF EXEMPLARY EMBODIMENTS

This specification describes exemplary embodiments and applications of the invention. The invention, however, is not limited to these exemplary embodiments and applications or to the manner in which the exemplary embodiments and applications operate or are described herein. Moreover, the Figures may show simplified or partial views, and the dimensions of elements in the Figures may be exaggerated or otherwise not in proportion for clarity. In addition, as the terms "on" and "attached to" are used herein, one object (e.g., a material, a layer, a substrate, etc.) can be "on" or "attached to" another object regardless of whether the one object is directly on or attached to the other object or there are one or more intervening objects between the one object and the other object. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

Figure 1:
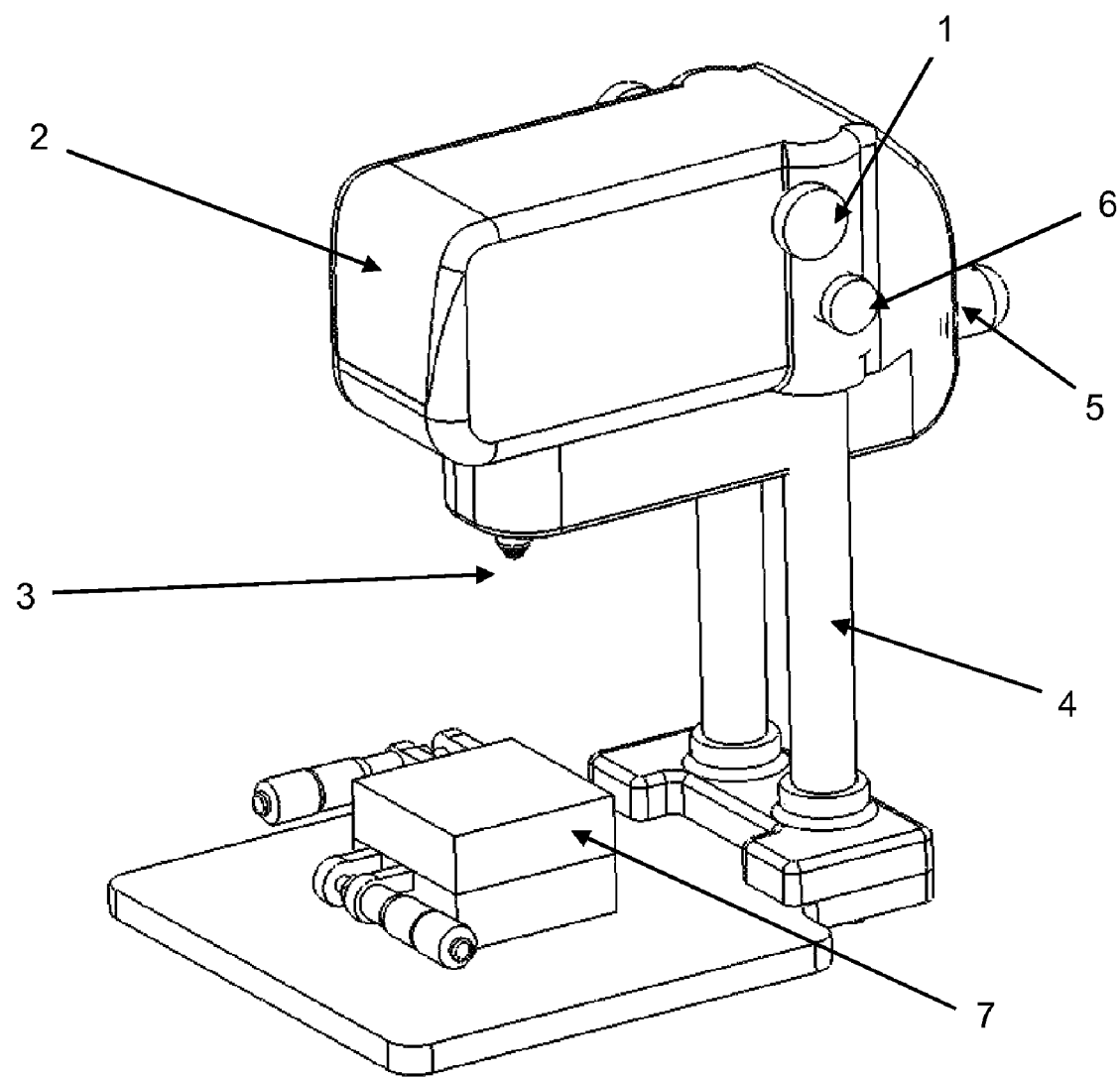
FIG. 1: A view of the exterior of an exemplary embodiment of an ophthalmic microscope is shown.
Figure 2:
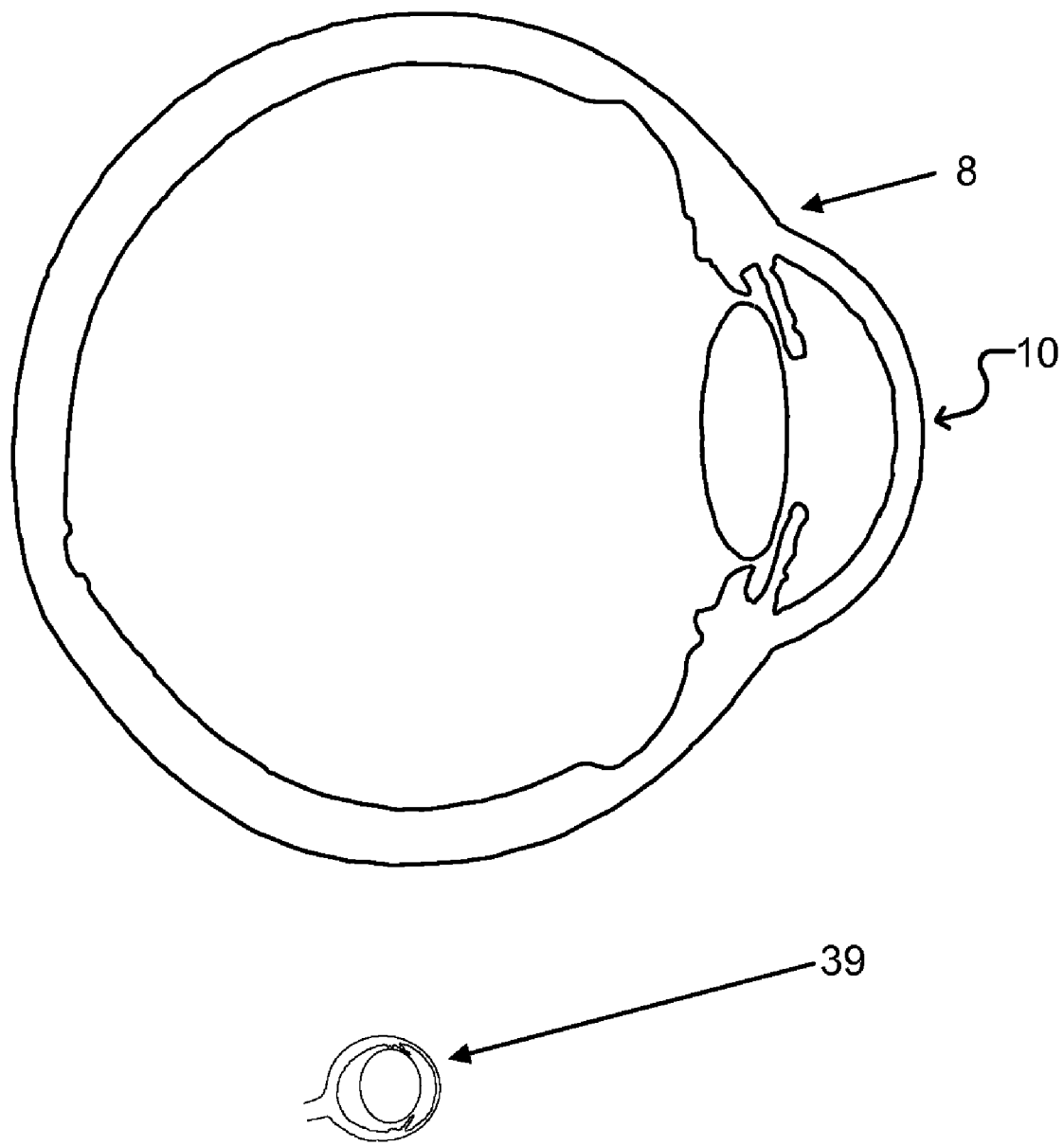
FIG. 2: A comparison of the size and structure of the rodent and human eye is shown at the same dimensional scale.
Figure 3:
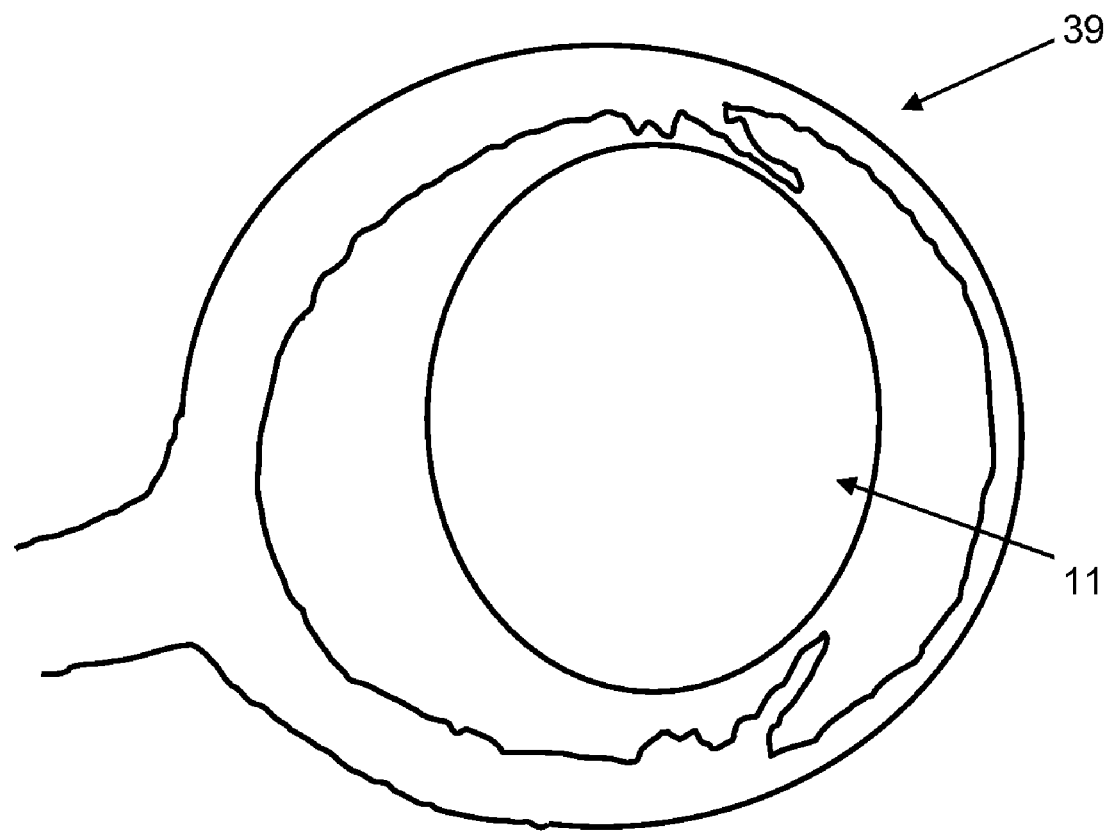
FIG. 3: A schematic of the mouse eye is shown on an enlarged scale to portray the optical structure of the eye.

In FIG. 1 is shown the exterior of an exemplary embodiment. With the object plane for a mouse eye mouse being approximately 2 millimeters in diameter and the resolution being 5 microns or better the system can more resemble a microscope than a standard eye camera. The animal can be placed on a stage 7 after being anaesthetized. This stage 7 can provide for precise transverse adjustment of the animal's position under the objective lens 3 and the stand 4 can stabilize the system in the vertical motion. The vertical adjustment knob 1 can be used to lower the body of the imaging system 2 down until the objective lens 3 just touches the animal's eye. A transparent gel such as Goniosol can be placed on the eye to facility optical coupling.

The knobs 6 can provide for course and fine focus of the image. The illumination light can be fed to the illumination tube 5 from a separate box through a fiber optic and the imaging system body and image sensor can be located in housing 2. The exciter filters for angiography or auto-fluorescent imaging can be located in the illumination tube 5 and the barrier filter can be located inside the body 2.

Figure 4:
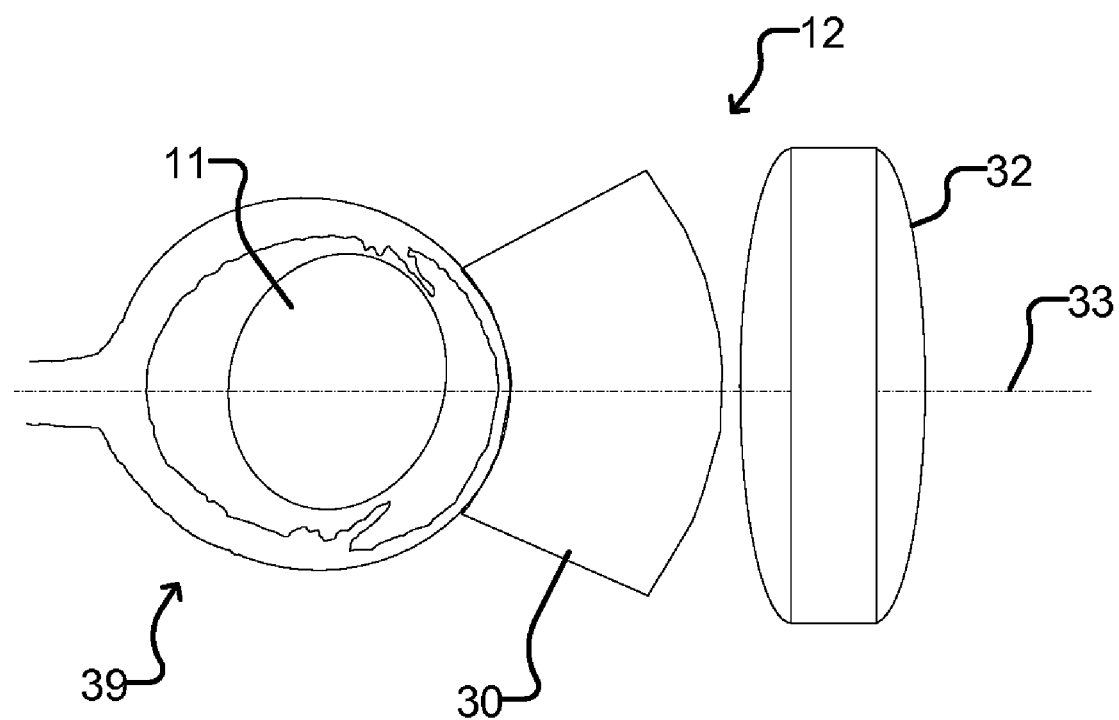
FIG. 4: An exemplary design of an objective lens set is shown.

A difference with rodent eyes as compared to the human eye is the small f-number and physical size. In this description, the dimensions discussed are for the mouse eye, but for the rat eye, transverse dimensions are approximately doubled. In FIG. 4 is a front or objective lens set 12 of the imaging system. The objective lens set 12 (which can be the objective lens 3 of FIG. 1) can comprise a contact lens 30. The contact lens 30 contacts the eye 39 of the animal. For example, the animal can be a mouse or a rat, and contact lens 30 can be sized to contact a mouse eye or a rat eye. The use of a contact lens 30 to contact the mouse or rat eye can provide alignment and stabilization. And, by contacting the eye aberrations of the cornea can be essentially eliminated. In some embodiments, a transverse alignment of better than 0.1 millimeters can be sought. With the relatively large pupil of mouse and rat eyes we can inject the light through the marginal area of the rodent eye pupil. For example, as discussed below, the light can be injected into the rodent eye as a ring of light at an outer portion of the rodent's pupil. The objective lens set 12 can be interchangable, and different lens sets optimized for different eyes can be utilized. That is, the imaging system can be configured such that the objective lens set 12 can be readily removed and replaced with a different objective lens set 12 optimized for different use with different animals or for different imaging functions. For example, one objective lens set 12 can be configured for imaging an eye of a mouse, and a different objective lens set 12 can be configured for imaging an eye of a rat. Still other objective lens sets 12 can be configured for imaging an eye of other animals (e.g., rabbits, monkeys, etc.). The imaging system can thus be used to image an eye of different animals simply by replacing the objective lens set 12.

Figure 6A:
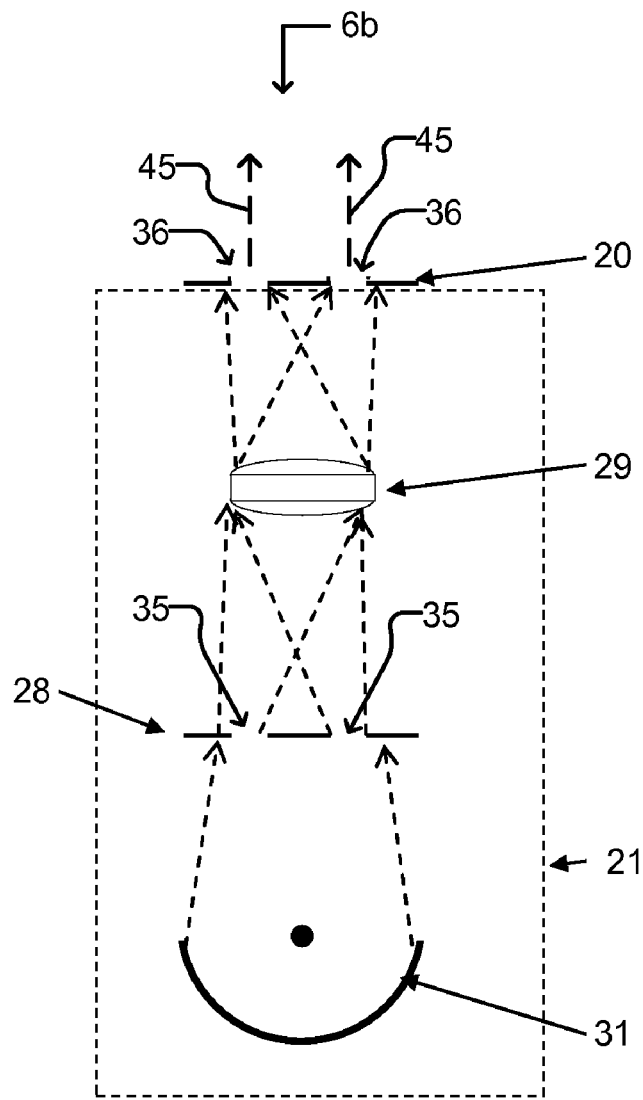
FIG. 6a: A schematic diagram of an example of the module for generating light of the system of FIG. 5 is shown.
Figure 6B:
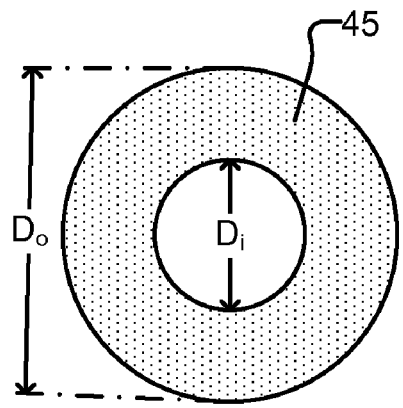
Figure 6C:
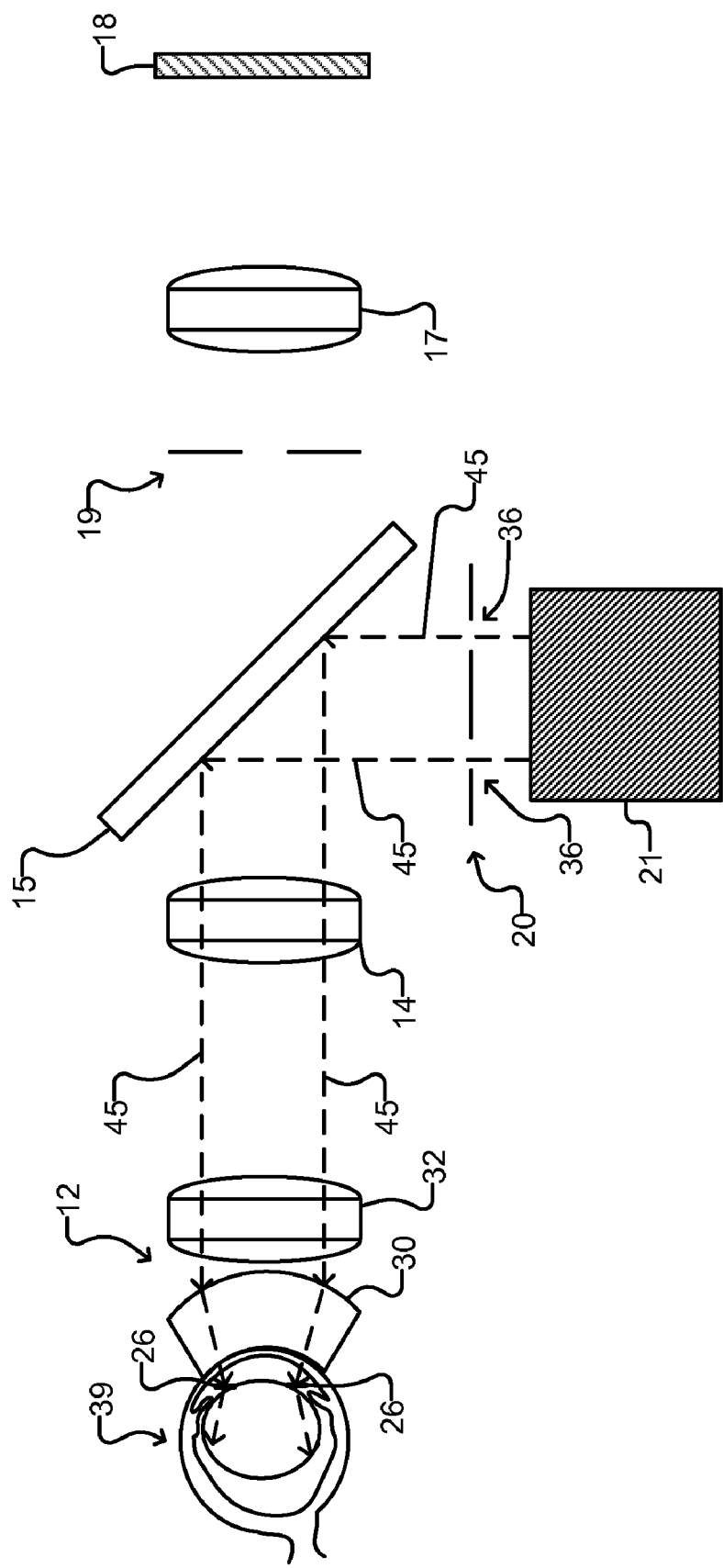
FIG. 6c: Illustrates generation and projection of a light ring to the eye in the system of FIG. 5.

FIG. 5 illustrates an exemplary configuration of an imaging system that can be used in the microscope of FIG. 1. As shown, following the objective lens set 12 can be such optics as perform the function of injection of the illumination light into the eye and relay the first image 13 to the second image 16 at the image sensor 18 and perform certain light filtering functions to assure high contrast imaging. As shown in FIG. 5, such optics can include a module 21 that generates light, which can be projected through an annular stop 20, reflected off of a partially reflecting mirror 15 (which can be a mirror that reflects for example 50% of the incident light and transmits 50% of the light) through relay lens 14 to the objective lens set 12, which can inject the light into the eye 39. Mirror 15 can partially reflect other percentages of light. For example, mirror 15 can reflect less than 50% and transmit more than 50% of incident light, or mirror 15 can reflect more than 50% and transmit less than 50% of incident light. Moreover, mirror 15 can take other configurations. For example, mirror 15 can be a full reflective mirror with a hole (not shown) sufficiently large to allow light 46 to pass through the hole (not shown) in the mirror 15. The hole (not shown) in the mirror 15, however, can be smaller than the generated light ring 45 output by the source 21 so that the ring 45 reflects off of the mirror 15 to the objective lens set 12 as shown in FIG. 6c. As another example mirror 15 can alternatively be a beam splitter. Lenses 30 and 32 together focus the light reflected from the interior of the back of the eye 39 to form a first image 13 of the back of the eye. Relay lens 14 can relay the light through mirror 15 and stop 19 (which can be a Lyot stop) to lens 17, which can focus the light to form a second image 16 of the back of the eye 39 at an image sensor 18. Optical axis 34 represents the optical axis of the light generated by source 21, and optical axis 33 represents the optical axis of the lenses 30, 32, 14, and 17.

Figure 7:
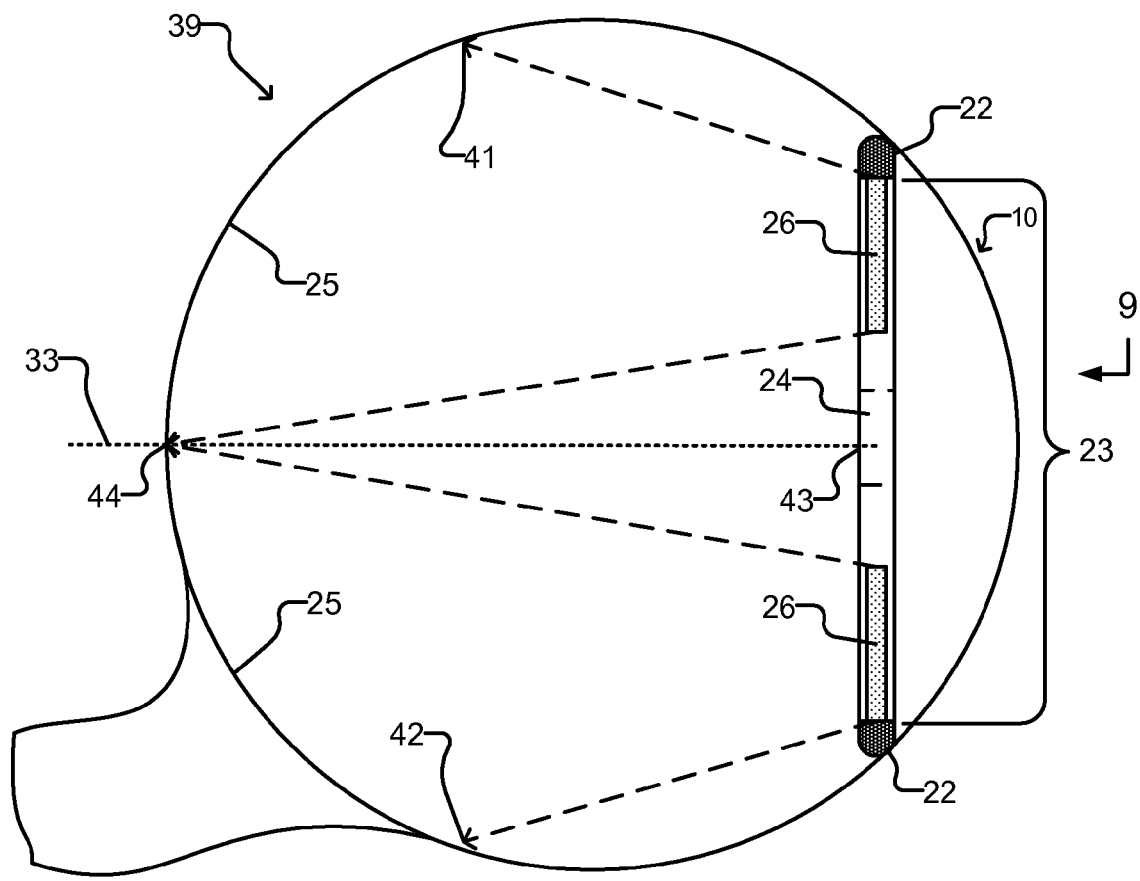
FIG. 7: Illustrates injection of the light ring of FIG. 6c into the eye.
Figure 8:
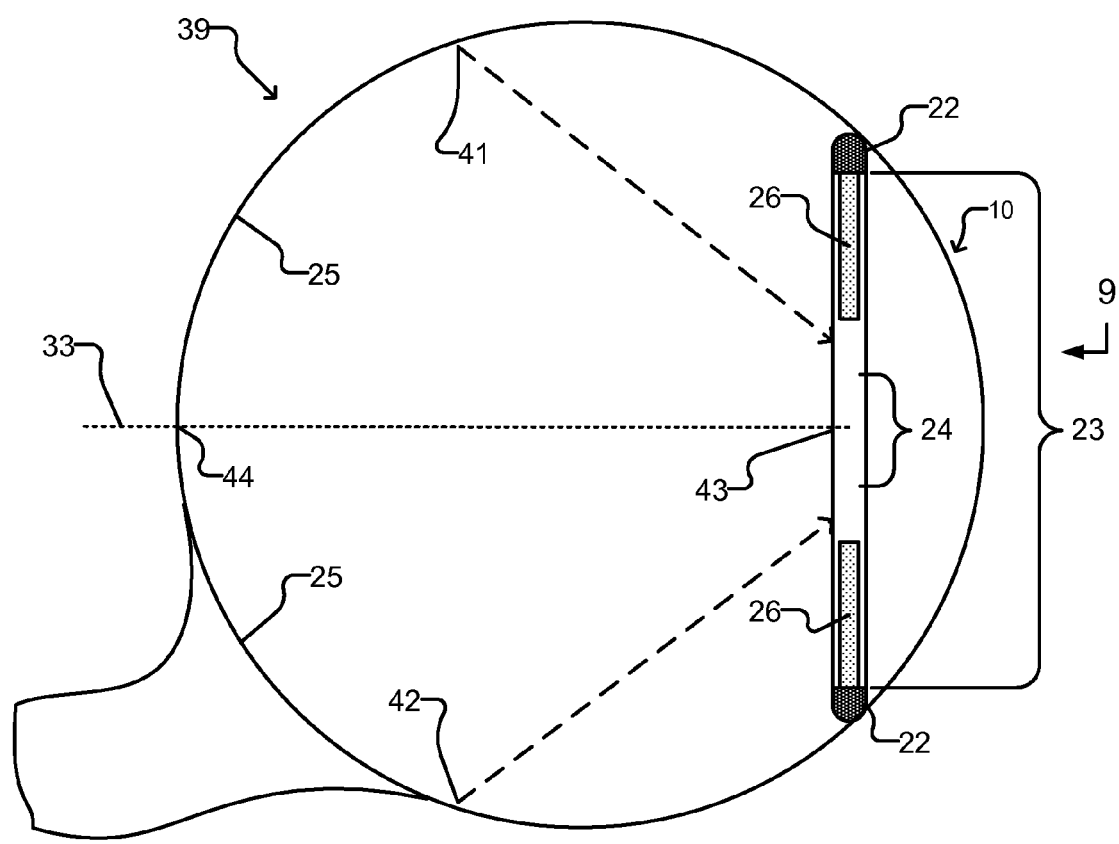
FIG. 8: Illustrates reflection of the injected light of FIG. 7 off of the back of the eye and out an exit pupil.
Figure 9:
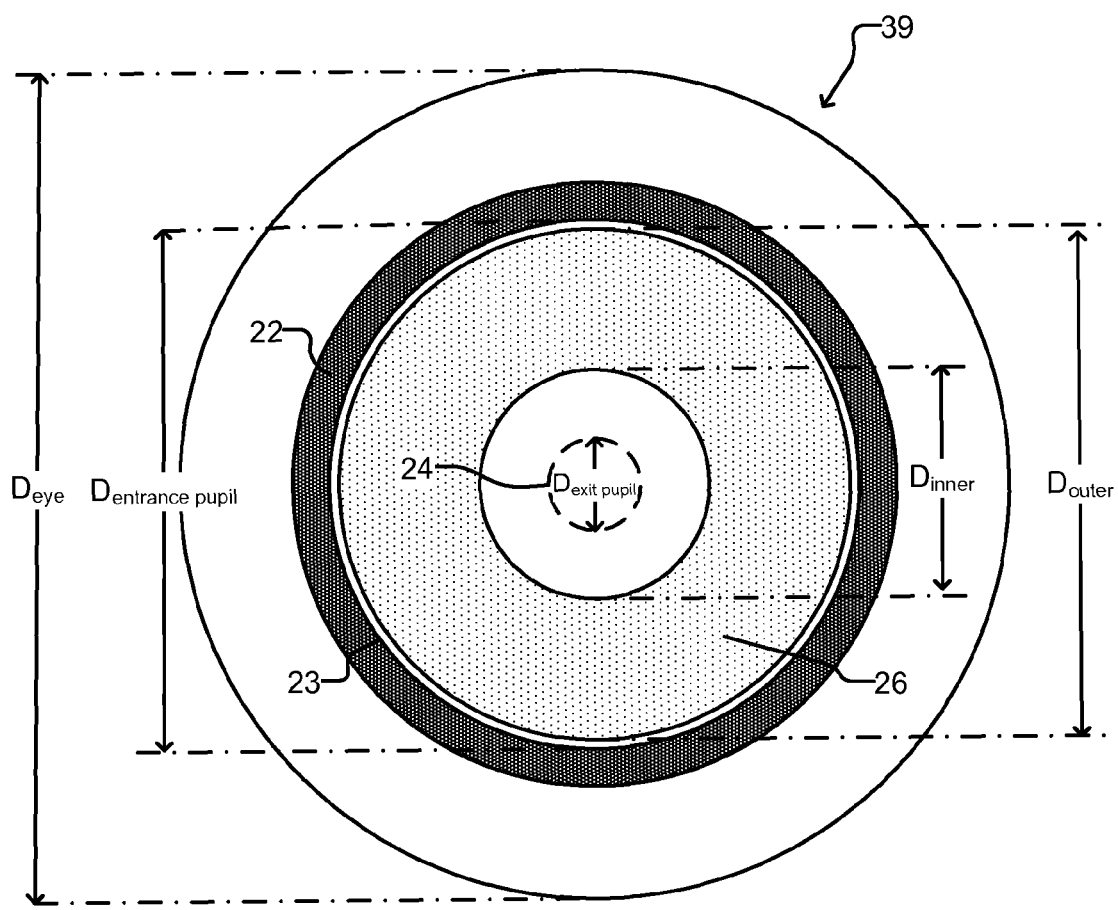
FIG. 9: Illustrates a front view of the eye of FIGS. 7 and 8.
Figure 10:
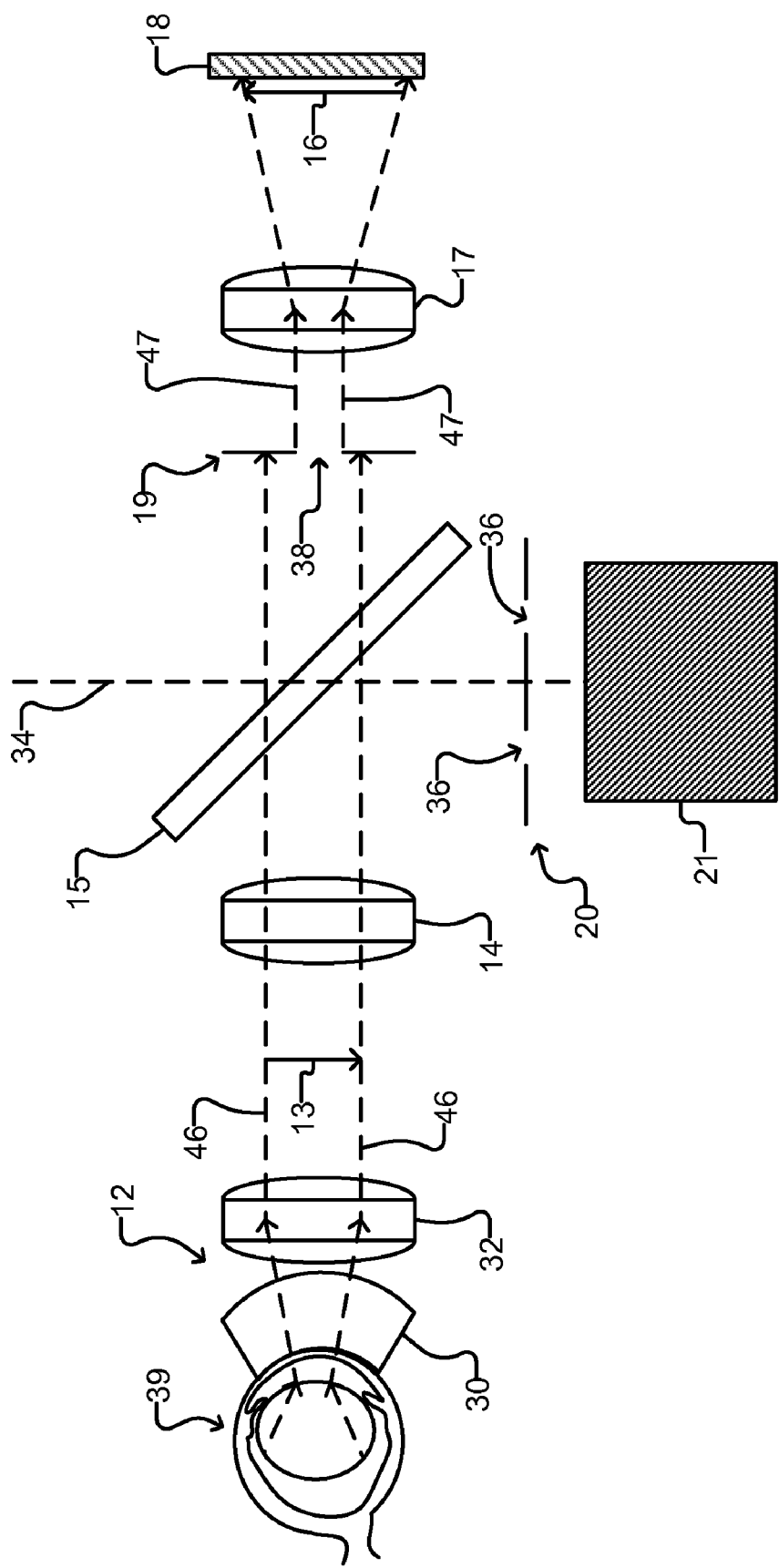
FIG. 10: Illustrates projection of the light reflected off of the back of the light and out the exit pupil (as shown in FIG. 8) to an imaging sensor.

Exemplary operation of the imaging system of FIG. 5 will now be discussed with respect to FIGS. 6a-6c and 7-10. As discussed in more detail below, FIG. 6a illustrates generation of a light ring 45 by source 21 of the system of FIG. 5, and FIG. 6b shows a front view of the generated light ring 45. FIG. 6c illustrates projection by the system of FIG. 5 of the generated light ring 45 to objective lens set 12 and into eye 39 as injected light ring 26. FIG. 7 illustrates a detailed view of eye 39 of FIG. 6c showing injection of the generated light ring 45 (as injected light ring 26) by relay lens 14 and objective lens set 12 into eye 39. FIG. 8 illustrates the same detailed view of eye 39 as is shown in FIG. 8 but showing reflection of the injected light ring 26 off the back 25 of the eye 39 and out an exit pupil 24. FIG. 9 shows a front view of the eye 39 taken from FIGS. 8 and 9. FIG. 10 shows how the system of FIG. 5 collects light reflected from the back 25 of the eye 39 and forms a first image 13 and a second image 16 at an image sensor 18. A detailed discussion of FIGS. 6a-6c and 7-10 now follows.

FIG. 6a shows an exemplary embodiment of module 21 of FIG. 5. As shown in FIG. 6a light (indicated by dashed lines) can be generated by source 31 and focused on an annular stop 28, which can have an opening 35 in the form of a ring. Source 31 can be any source of light. For example, source 31 can be a source of white light (e.g., source 31 can be a Xenon lamp). The light exiting stop 28 can pass through lens 29 and can be re-imaged by lens 29 onto a mask 20. The lens diameter and focal length of lens 29 can be selected to control the beam vergence whereas the stop 28 can determine the size and shape of the beam.

Referring again to FIG. 6a the light generated and conditioned by module 21 can be projected onto mask 20. Mask 20 can have an opening 36 in the form of a ring so that light exiting the mask 20 through opening 36 is in the form of a ring as shown in FIG. 6b, which shows a front view of generated light ring 45 exiting opening 36 in mask 20. The generated light ring 45 can be a different size than the injected light ring 26, although the injected light ring 26 can be proportional to the generated light ring 45. This is because relay lens 14 and the objective lens set 12 can magnify (e.g., make larger (positive magnification) or smaller (negative magnification)) the generated light ring 45 to thereby produce the injected light ring 26. In such a case, the outer diameter $D_o$ and the inner diameter $D_i$ of the generated light ring 45 can be proportional to the dimensions specified as $D_{outer}$ and $D_{inner}$ in Tables 1, 2, 3, and/or 4 below. Alternatively, the generated light ring 45 and the injected light ring 26 can be the same size. In such a case, the outer diameter $D_o$ and inner diameter $D_i$ of the generated ring 45—and thus the opening 36—can have the dimensions specified as $D_{outer}$ and $D_{inner}$ in Tables 1, 2, 3, and/or 4 below.

As shown in FIG. 6c, the generated light ring 45 exiting the opening 36 in mask 20 can be reflected by the partial mirror 15 and refocused into the eye 39 near a plane of the iris 22 of the eye. In contrast to conventional eye imaging systems, the generated light ring 45 can be passed through the imaging and relay optics (e.g., 12, 14) as opposed to being projected through air or in a fiber beam around the outside of the imaging optics. For example, as shown in FIG. 6c, the generated light ring 45 can be directed through contact lens 30 into eye 39. In fact, the generated light ring 45 can be directed through the relay lens 14 and the objective lens set 12 into eye 39.

FIGS. 7-9 illustrate the injection of the generated light ring 45 into the eye 39 and reflection of the light off of the back 25 of the eye and out of the eye 39.

FIG. 7 shows a simplified side, cross-sectional view of the eye 39 illustrating injection of the generated light ring 45 into the eye 39. As discussed above, the generated light ring 45 can be magnified by the relay lens 14 and objective lens set 12 (see FIG. 6c), and thus can be reduced (or increased) in size. Alternatively, the generated light ring 45 need not be magnified by the lens 14 and objective lens set 12, and can thus be the same size as the generated light ring 45. As projected onto a plane of the iris 22 in FIG. 7 (and FIGS. 8 and 9) by the relay lens 14 and objective lens set 12, the ring of light injected into the eye 39 is labeled 26 (because, as mentioned above, light ring 26 can be a different size than generated light ring 45). As shown, the injected light ring 26 enters the eye 39 through an entrance pupil 23, which can be the portion of the eye 39 within the inner diameter of the iris 22. The eye 39 can be dilated to increase the size of the entrance pupil 23. The injected light ring 26 can strike the back 25 of the eye 39.

Points 41 and 42 illustrate points in the cross-sectional view of FIG. 7 between which the injected light ring 26 illuminates the back 25 of eye 39. That is, the injected light ring 26 entering the eye 39 can illuminate the back 25 of the eye 39 between points 41 and 42 in FIG. 7. In some embodiments, an angle between an axis 33 along which the incoming injected light ring 26 is directed and a line segment between point 43 and point 41 can be as much as thirty-five degrees. Such an angle can, of course, be smaller (e.g., thirty, twenty-five, twenty, or fifteen degrees or any angle in between the foregoing angles). Similarly, an angle between axis 33 and a line segment between point 43 and point 42 can be as much as thirty-five degrees, although the angle can be smaller (e.g., thirty, twenty-five, twenty, or fifteen degrees or any angle in between the foregoing angles). Point 43 can be where axis 33 crosses the entrance pupil 23.

The injected light ring 26 can reflect off the back 25 of the eye 39. FIG. 8 illustrates an example. As shown in FIG. 8 (which shows the same detailed view of eye 39 as is shown in FIG. 7), the injected light ring 26 injected into the eye 39 (as shown in FIG. 7) reflects off of the back 25 of the eye 39. As also shown in FIG. 8, the light (shown as dashed lines in FIG. 8) that reflects off of the back 25 of the eye 39 can exit the eye 39 through the central opening in (i.e., within an inner diameter of) the injected light ring 26. The contrast of the resulting image of the back 25 of the eye 39, however, can be improved by utilizing less than all of the light that exits the eye 39 through the central opening in the injected light ring 26. As will be discussed, this can be accomplished by blocking (e.g., with stop 19 in FIG. 10) some of the exiting light such that only reflected light that exists eye 39 through an effective exit pupil 24 within the inner diameter of the injected light ring 26 is actually used to generated the image of the back 25 of the eye 39.

FIG. 9, which shows a front view of the eye 39, illustrates exemplary relationships among the eye 39, the iris 22, the entrance pupil 23, the injected light ring 26, and the exit pupil 24. In FIG. 9, the diameter of the eye 39 is labeled $D_{eye}$, the diameter of the entrance pupil 23 is labeled $D_{entrance\ pupil}$, the outer diameter of the injected light ring 26 is labeled $D_{outer}$, the inner diameter of the injected light ring 26 is labeled $D_{inner}$, and the diameter of the effective exit pupil 24 is labeled $D_{exit\ pupil}$. As mentioned, the eye 39 can be dilated to maximize the diameter $D_{entrance\ pupil}$ of the entrance pupil 23 to allow the illumination ring's 26 outer diameter $D_{outer}$ to be maximized. The diameter $D_{entrance\ pupil}$ of the entrance pupil 23 is effectively the inner diameter of the iris 22. The outer diameter $D_{outer}$ of the illumination ring 26 can be set to be just smaller than the diameter $D_{entrance\ pupil}$ of the entrance pupil 23. The inner diameter $D_{inner}$ of the illumination ring 26 is set to be larger than the diameter $D_{exit\ pupil}$ of the effective exit pupil 23, which as discussed above is a relayed image (or is defined by) the opening 38 in stop 19. Because of the large dilation of the rodent iris 22 (and thus the large diameter $D_{entrance\ pupil}$ of the entrance pupil 23) as a fraction of the diameter $D_{eye}$ of the eye 39, the diameter $D_{exit\ pupil}$ of the exit pupil 24 can be set to be larger as a fraction of the eye 39 diameter $D_{eye}$ and the illumination ring 26 can also have a larger physical area.

With the inner diameter $D_{inner}$ of the illumination ring 26 at the entrance pupil 22 being larger than the diameter $D_{exit\ pupil}$ of the exit pupil 23, separation of the imaging light arising from reflections and scattering from the back 25 of the eye 39 from scattered light from the crystalline lens 11 can be excellent and unwanted reflections and scattering from optical elements can be reduced as well. As mentioned, because of the large dilation of the rodent eye 39 the outer diameter $D_{outer}$ of the illumination ring 26 can be a large fraction of the diameter $D_{eye}$ of the eye 39 whereas with the human eye 8 the illumination ring is a small fraction of the eye diameter. This allows the exit pupil 24 to be a larger fraction of the diameter $D_{eye}$ of the eye 39 and allows smaller f numbers. Since the resolution of an optical system is at best approximately the f number times the wavelength this allows resolutions with the rodent eye 39 below 5 microns.

Table 1 nominates exemplary dimensions for the eye 39 of a mouse.

TABLE 1

| Identifier in FIG. 9 | Approximate dimension |
|---|---|
| $D_{eye}$ | 3 millimeters |
| $D_{entrance\ pupil}$ | 2 millimeters |
| $D_{outer}$ | 1.55 millimeters |
| $D_{inner}$ | 0.82 millimeters |
| $D_{exit\ pupil}$ | 0.33 millimeters |

It should be apparent that the size of the ring 26 compared to the diameter $D_{eye}$ of the eye 39 of a mouse is relatively large. For example, a ratio of the difference between the outer and inner diameters of the ring 26 and the diameter of the eye 39 of a mouse (corresponding to the formula $([D_{outer}-D_{inner}]/D_{eye})$ can be about twenty-five percent in some embodiments. As discussed below, the dimensions in Table 1 are exemplary only, and other dimensions are possible. Consequently, the ratio of the difference between the outer and inner diameters of the ring 26 and the diameter of the eye 39 of a mouse can be other than twenty-five percent (e.g., that ratio can be 15%, 20%, 30%, 35%, 40%, 45%, or any ratio or percentage between the foregoing). The relatively large size of the ring 26 as a percentage or ratio of the diameter $D_{eye}$ of the eye 39 can be important. For example, the relatively large size of the ring 26 as a percentage or ratio of the diameter $D_{eye}$ of the eye 39 can increase the amount of light that can be injected into the eye 39, which can allow for generation of an image of the back 25 of the eye 39 using standard (those typically used in eye imaging devices) light sources as the source 31 (see FIG. 6a). For example, standard Xenon lamps can be used as a source 31. Moreover, because a mouse eye can be dilated to an F number of about f1.3 (where f is the effective focal length of the camera, and the F number is the focal length (f) divided by the diameter $D_{entrance\ pupil}$ of the entrance pupil), using lamps such as the foregoing, sufficient light can be injected into the eye 39 to generate images, in some embodiments, having resolutions of as fine as five microns. In other embodiments, images with a resolution as fine as two microns can be generated. In addition to allowing the use of standard lamps and facilitating high resolution images, the above described ratios can also facilitate generating images with a wide field of view and color images.

As can be determined from the dimensions of Table 1, the ratio of the diameter $D_{exit\ pupil}$ of the exit pupil 24 to the inner diameter $D_{inner}$ of the injected light ring 26 for a mouse eye can be about 0.4. That is, for a mouse eye, an area of the exit pupil 24 can be about 40% of the area enclosed by the inner diameter $D_{inner}$ of the injected light ring 26. As discussed below, the dimensions in Table 1 are exemplary only, and other dimensions are possible. Consequently, the ratio of the diameter $D_{exit\ pupil}$ of the exit pupil 24 to the inner diameter $D_{inner}$ of the injected light ring 26 for a mouse eye can be other than 0.4 (or 40%). For example, the ratio of the diameter $D_{exit\ pupil}$ of the exit pupil 24 to the inner diameter $D_{inner}$ of the injected light ring 26 for a mouse eye can be about 0.25 (or 25%), 0.3 (or 30%), 0.35 (or 35%), 0.45 (or 45%), 0.5 (or 50%), 0.55 (or 55%), 0.6 (or 60%), 0.65 (or 65%), 0.7 (or 70%), or 0.75 (or 75%) or any ratio or percentage between any of the foregoing. That the diameter $D_{exit\ pupil}$ of the exit pupil 24 is smaller than the inner diameter $D_{inner}$ of the injected light ring 26 by the above-mentioned ratios can be important because this can result in a higher quality image of the eye 39. This can be because most of the scattered light or other errant light reflected through the eye 39 exits the eye 39 through the margin between the exit pupil 24 and the inner diameter $D_{inner}$ of the injected light ring 26. By utilizing only light reflected through an exit pupil 24 that is smaller than the inner diameter $D_{inner}$ of the injected light ring 26 by the above-mentioned ratios, the scattered and other errant light in the margin between the exit pupil 24 and the inner diameter $D_{inner}$ of the injected light ring 26 can be blocked (e.g., by the stop 19 as discussed below) and not used to form the image 16 of the eye 39, improving the quality of the image 16.

The dimensions in Table 1 above are approximate and exemplary, and the invention is not limited to those dimensions. For example, each of the foregoing dimensions can alternatively be within a range that is between about seventy-five percent (75%) and about one hundred twenty-five (125%) percent of the given dimension. The following table provides exemplary ranges for an eye 39 of a mouse:

TABLE 2

| Identifier in FIG. 9 | Dimension range |
|---|---|
| $D_{eye}$ | 2.25-3.75 millimeters |
| $D_{entrance\ pupil}$ | 1.5-2.5 millimeters |
| $D_{outer}$ | 1.1-1.9 millimeters |
| $D_{inner}$ | 0.6-1.0 millimeters |
| $D_{exit\ pupil}$ | 0.2-0.4 millimeters |

The following table provides typical, approximate values for the dimensions shown in FIG. 9 for a rat eye 39:

TABLE 3

| Identifier in FIG. 9 | Approximate dimension |
|---|---|
| $D_{eye}$ | 6 millimeters |
| $D_{entrance\ pupil}$ | 4 millimeters |
| $D_{outer}$ | 3.1 millimeters |
| $D_{inner}$ | 1.64 millimeters |
| $D_{exit\ pupil}$ | 0.66 millimeters |

It should be apparent that, for a rat, the size of the ring 26 compared to the diameter of the eye 39 is relatively large. For example, a ratio of the difference between the outer and inner diameters of the ring 26 and the diameter of the eye 39 (corresponding to the formula $([D_{outer}-D_{inner}]/D_{eye})$ can be about twenty-five percent in some embodiments. As discussed below, the dimensions in Table 3 are exemplary only, and other dimensions are possible. Consequently, the ratio of the difference between the outer and inner diameters of the ring 26 and the diameter of the eye 39 for a rat can be other than twenty-five percent (e.g., that ratio can be 15%, 20%, 30%, 35%, 40%, 45%, or any ration or percentage between the foregoing.). As generally discussed above, the relatively large size of the ring 26 as a percentage or ratio of the diameter $D_{eye}$ of the eye can be important. For example, the relatively large size of the ring 26 as a percentage or ratio of the diameter $D_{eye}$ of the eye or a rat can increase the amount of light that can be injected into the eye, which can allow for generation of an image of the back 25 of the eye 39 using standard (those typically used in eye imaging devices) light sources as the source 31 (see FIG. 6a). For example, standard Xenon lamps can be used as source 31. Generally in accordance with the discussion above, because an eye 39 of a rat can be dilated to an F number of about f1.3 using lamps such as the foregoing, sufficient light can be injected into the eye 39 of a rat to generate images, in some embodiments, having resolutions of as fine as five microns. In other embodiments, images with a resolution as fine as two microns can be generated. In addition to allowing the use of standard lamps and facilitating high resolution images, the above described ratios can also facilitate generating images with a wide field of view and color images.

As can be determined from the dimensions of Table 3, the ratio of the diameter $D_{exit pupil}$ of the exit pupil 24 to the inner diameter $D_{inner}$ of the injected light ring 26 for the rat eye can be about 0.4. That is, an area of the exit pupil 24 can be about 40% of the area enclosed by the inner diameter $D_{inner}$ of the injected light ring 26. As discussed below, the dimensions in Table 3 are exemplary only, and other dimensions are possible. Consequently, the ratio of the diameter $D_{exit pupil}$ of the exit pupil 24 to the inner diameter $D_{inner}$ of the injected light ring 26 for a rat eye can be other than 0.4 (or 40%). For example, the ratio of the diameter $D_{exit pupil}$ of the exit pupil 24 to the inner diameter $D_{inner}$ of the injected light ring 26 for a rat eye can be about 0.25 (or 25%), 0.3 (or (30%), 0.35 (or 35%), 0.45 (or 45%), 0.5 (or 50%), 0.55 (or (55%), 0.6 (or 60%), 0.65 (or 65%), 0.7 (or 70%), or 0.75 (or 75%) or any ratio between any of the foregoing ratios. That the diameter $D_{exit pupil}$ of the exit pupil 24 is smaller than the inner diameter $D_{inner}$ of the injected light ring 26 by the above-mentioned ratios can be important because this can result in a higher quality image of the eye 39. This can be because most of the scattered light or other errant light reflected through the eye 39 exits the eye 39 through the margin between the exit pupil 24 and the inner diameter $D_{inner}$ of the injected light ring 26. By utilizing only light reflected through an exit pupil 24 that is smaller than the inner diameter $D_{inner}$ of the injected light ring 26 by the above-mentioned ratios, the scattered and other errant light in the margin between the exit pupil 24 and the inner diameter $D_{inner}$ of the injected light ring 26 can be blocked (e.g., by the stop 19 as discussed below) and not used to form the image 16 of the eye 39, improving the quality of the image 16.

The dimensions in Table 3 above are approximate and exemplary, and the invention is not limited to those dimensions. For example, each of the foregoing dimensions can be within a range that is between seventy-five percent (75%) and one hundred twenty-five (125%) percent of the give dimension. The following table provides exemplary ranges:

TABLE 4

| Identifier in FIG. 9 | Dimension range |
| --- | --- |
| $D_{eye}$ | 4.5-7.5 mm |
| $D_{entrance pupil}$ | 3-5 mm |
| $D_{outer}$ | 2.2-3.8 mm |
| $D_{inner}$ | 1.2-2.0 mm |
| $D_{exit pupil}$ | 0.4-0.8 mm |

FIG. 10 shows the light reflected off of the back 25 of the eye 39 and out of the eye as image light 46. As shown, the system can create, from the image light 46, a first image 13 of the back 25 of the eye 39, which can be relayed by relay lens 14 through mirror 15 and stop 19 to lens 17. The stop 19 can have an opening 38 whose diameter is smaller than the relayed image 13. Thus, any scattered light in the relayed image 13 can be blocked by stop 19. The size of the opening 38 in stop 19 effectively defines the size of exit portion 24 in FIG. 8. Put another way, the opening 38 in the stop 19 can block all of the reflected light that exits the eye 39 through the space defined by the inner diameter $D_{inner}$ of the injected light ring 26 except for the reflected light that exits through the exit pupil 24 (see FIGS. 7-9). The opening 38 in stop 19 can be sized and positioned such that the reflected light that exits through the exit pupil 24 shown in FIGS. 7-9 passes through the opening 38. The exit pupil 24 can thus be the size of the opening 38. Alternatively, if the object lens set 12 and/or the lens 14 magnifies the light that exits the eye 39 through the exit pupil 24, the size of the exit pupil 24 can be proportional (e.g., by the magnification power (which can be positive or negative) of the objective lens set 12 and/or lens 14 to the size of the opening 38 in stop 19. The portion of the image light 46 that passes through opening 38 in stop 19 is labeled 47 in FIG. 10. As shown, lens 17 can focus the image light 47 that passes through the opening 38 in the stop 19 to form a second image 16 on an image sensor 18. Focusing of image 16 can be accomplished by movement of the image sensor 18 in the direction of the optical axis 33 (see FIG. 5). Stop 19 is exemplary only, and other types of blocking mechanisms can be used to pass only light reflected through exit pupil 24, blocking all other light.

Image sensor 18 can be configured to create a viewable image (e.g., on a projection screen (not shown)) of the back 25 of the eye 39 or create a digital image of the back 25 of the eye 39 and store the digital image in a digital memory device (not shown), which can be a semiconductor based memory device, an optical based memory device, or a magnetic based memory device. Such a stored image can be later retrieved from the memory device and displayed on a computer screen or printed. As yet another alternative, image sensor 18 can create a physical photograph of the back 25 of the eye 39. A computer or computers (not shown) can be used with the image sensor 18 to create, store, print, generate a photograph, etc. of the image 16 of the back 25 of the eye 39.

Although specific embodiments and applications of the invention have been described in this specification, these embodiments and applications are exemplary only, and many variations are possible.

I claim:

1. A method of imaging an eye of a rodent, the method comprising:
    injecting a ring of light through an outer portion of an entrance pupil of the eye of the rodent onto a back interior portion of the eye;
    collecting light reflected off of the back interior portion of the eye and through an exit pupil effectively located at the entrance pupil within the ring of light, a diameter of the exit pupil at the entrance pupil being less than an inner diameter of the ring of light; and
    focusing the collected light reflected off of the back interior portion of the eye and thereby forming an image of the back interior portion of the eye,
    wherein a difference between an outer diameter of the ring and the inner diameter of the ring at the entrance pupil is at least thirty-five percent of a diameter of the eye.

2. The method of claim 1, wherein the difference between the outer diameter of the ring and the inner diameter of the ring is at least forty percent of the diameter of the eye.

3. The method of claim 1, wherein the rodent is a mouse.

4. The method of claim 3, wherein:
    the outer diameter of the ring projected through the entrance pupil is between 1.1 millimeters and 1.9 millimeters;

the inner diameter of the ring projected through the entrance pupil is between 0.6 millimeters and 1.0 millimeters; and the diameter of the eye is between 2.25 millimeters and 3.75 millimeters.

5. The method of claim 3, wherein:
the outer diameter of the ring projected through the entrance pupil is about 1.55 millimeters;
the inner diameter of the ring is about 0.82 millimeters; and
the diameter of the eye is about 3 millimeters.

6. The method of claim 1, wherein the rodent is a rat.

7. The method of claim 6, wherein:
the outer diameter of the ring projected through the entrance pupil is between 2.2 millimeters and 3.8 millimeters;
the inner diameter of the ring projected through the entrance pupil is between 1.2 millimeters and 2.0 millimeters; and
the diameter of the eye is between 4.5 millimeters and 7.5 millimeters.

8. The method of claim 6, wherein:
the outer diameter of the ring projected through the entrance pupil is about 3.1 millimeters;
the inner diameter of the ring projected through the entrance pupil is about 1.64 millimeters; and
the diameter of the eye is about 6 millimeters.

9. The method of claim 1, wherein the injecting comprises:
generating a ring of light, and
projecting the generated ring of light through a lens into the eye.

10. The method of claim 9, wherein the lens is in contact with the eye.

11. The method of claim 10, wherein a contact portion of the contact lens that contacts the eye has a curvature that corresponds to a curvature of the eye.

12. The method of claim 1, wherein the focusing comprises focusing the collected light onto an image sensor.

13. The method of claim 1, wherein the outer diameter of the ring at the entrance pupil is at least fifty percent of the diameter of the eye.

14. The method of claim 1, wherein the difference between the outer diameter of the ring and the inner diameter of the ring at the entrance pupil is at least fifty percent of the diameter of the eye.

15. The method of claim 1, wherein the difference between the outer diameter of the ring and the inner diameter of the ring at the entrance pupil is at least sixty percent of the diameter of the eye.

16. The method of claim 1, wherein a diameter of the exit pupil at the entrance pupil is less than seventy percent of the inner diameter of the light ring at the entrance pupil.

17. The method of claim 1, wherein a diameter of the exit pupil at the entrance pupil is less than fifty percent of the inner diameter of the light ring at the entrance pupil.

18. The method of claim 1, wherein the outer diameter of the ring at the entrance pupil is at least forty percent of the diameter of the eye.

19. An apparatus for imaging an eye of a rodent, the apparatus comprising:
a light source configured to generate a ring of light;
a contact lens sized and configured to contact the eye of the rodent and inject the ring of light through an outer portion of an entrance pupil of the eye onto a back interior portion of the eye, wherein a difference between an outer diameter of the ring and an inner diameter of the ring at the entrance pupil is at least thirty-five percent of a diameter of the eye; and
an optical system configured to relay the ring of light generated by the light source to the contact lens, the optical system further configured to collect light reflected off of the back interior portion of the eye and through an exit pupil effectively located at the entrance pupil within the ring of light, a diameter of the exit pupil at the entrance pupil being less than an inner diameter of the ring of light, the optical system further configured to focus the collected light reflected off of the back interior portion of the eye and thereby form an image of the back interior portion of the eye.

20. The apparatus of claim 19, wherein the difference between the outer diameter of the ring and the inner diameter of the ring is at least forty percent of the diameter of the eye.

21. The apparatus of claim 19, wherein:
the outer diameter of the ring projected through the entrance pupil is between 1.1 millimeters and 1.9 millimeters;
the inner diameter of the ring projected through the entrance pupil is between 0.6 millimeters and 1.0 millimeters; and
the diameter of the eye is between 2.25 millimeters and 3.75 millimeters.

22. The apparatus of claim 19, wherein:
the outer diameter of the ring projected through the entrance pupil is about 1.55 millimeters;
the inner diameter of the ring projected through the entrance pupil is about 0.82 millimeters; and
the diameter of the eye is about 3 millimeters.

23. The apparatus of claim 19, wherein:
the outer diameter of the ring projected through the entrance pupil is between 2.2 millimeters and 3.8 millimeters;
the inner diameter of the ring projected through the entrance pupil is between 1.2 millimeters and 2.0 millimeters; and
the diameter of the eye is between 4.5 millimeters and 7.5 millimeters.

24. The apparatus of claim 19, wherein:
the outer diameter of the ring projected through the entrance pupil is about 3.1 millimeters;
the inner diameter of the ring projected through the entrance pupil is about 1.64 millimeters; and
the diameter of the eye is about 6 millimeters.

25. The apparatus of claim 19 further comprising an image sensor onto which the optical system focuses the reflected light.

26. The apparatus of claim 19, wherein a contact portion of the contact lens that contacts the eye has a curvature that corresponds to a curvature of the eye.

27. The apparatus of claim 19, wherein the outer diameter of the ring at the entrance pupil is at least fifty percent of the diameter of the eye.

28. The apparatus of claim 19, wherein the difference between the outer diameter of the ring and the inner diameter of the ring at the entrance pupil is at least fifty percent of the diameter of the eye.

29. The apparatus of claim 19, wherein the difference between the outer diameter of the ring and the inner diameter of the ring at the entrance pupil is at least sixty percent of the diameter of the eye.

30. The apparatus of claim 19, wherein a diameter of the exit pupil at the entrance pupil is less than seventy percent of the inner diameter of the light ring at the entrance pupil.

31. The apparatus of claim 19, wherein a diameter of the exit pupil at the entrance pupil is less than fifty percent of the inner diameter of the light ring at the entrance pupil.

32. The apparatus of claim 19, wherein the outer diameter of the ring at the entrance pupil is at least forty percent of the diameter of the eye.

* * * * *